United States Patent [19]

deBruyne et al.

[11] Patent Number: 4,760,028

[45] Date of Patent: Jul. 26, 1988

[54] BIOREACTOR APPARATUS WITH SURFACE AERATOR SCREEN

[75] Inventors: Norman A. deBruyne, Princeton, N.J.; Gregg S. Feldscher, Philadelphia; Gregory J. MacMichael, Morrisville, both of Pa.

[73] Assignee: Techne Incorporated, Princeton, N.J.

[21] Appl. No.: 889,406

[22] Filed: Jul. 25, 1986

[51] Int. Cl.[4] ............................................... C12M 1/02
[52] U.S. Cl. ..................... 435/316; 435/312; 261/91; 261/120; 366/316
[58] Field of Search ............... 210/242.2; 261/91, 120; 435/313, 315, 316, 312; 366/315, 316

[56] References Cited

U.S. PATENT DOCUMENTS

| | | | |
|---|---|---|---|
| 2,556,854 | 6/1951 | Spears et al. | 435/316 X |
| 3,273,865 | 9/1966 | White | 261/91 X |
| 4,512,666 | 4/1985 | O'Connell | 366/249 |
| 4,581,181 | 4/1986 | Nicholls | 261/91 |
| 4,603,021 | 7/1986 | Urso | 261/30 |

FOREIGN PATENT DOCUMENTS

| | | | |
|---|---|---|---|
| 46-6035 | 12/1971 | Japan | 261/92 |
| 10677 | of 1904 | United Kingdom | 261/120 |
| 862761 | 3/1961 | United Kingdom | 261/91 |

OTHER PUBLICATIONS

Handa et al., "On the Evaluation of Gas-Liquid Interfacial Effects on Hybridoma Viability in Bubble Column Reactors", from *Develop. Biol. Standard*, vol. 66, Abstract of pp. 241-253.

"Mammalian Cell Technology", edited by William G. Tilly, published by Buttersworth, Jul. 1986.

Primary Examiner—Samuel Scott
Assistant Examiner—Allen J. Flanigan
Attorney, Agent, or Firm—Mason, Fenwick & Lawrence

[57] ABSTRACT

A bioreactor for cell culture medium is provided including a flask for holding the culture medium, a screen at or just below the surface of the culture medium, a mover for the screen to cause it to move generally parallel to the surface of the culture medium, and an integral or separate impeller to cause circulation of the culture medium to the surface of the liquid culture medium. The screen is preferably on a float, and is connected to be driven at different levels of the liquid in the flask.

13 Claims, 2 Drawing Sheets

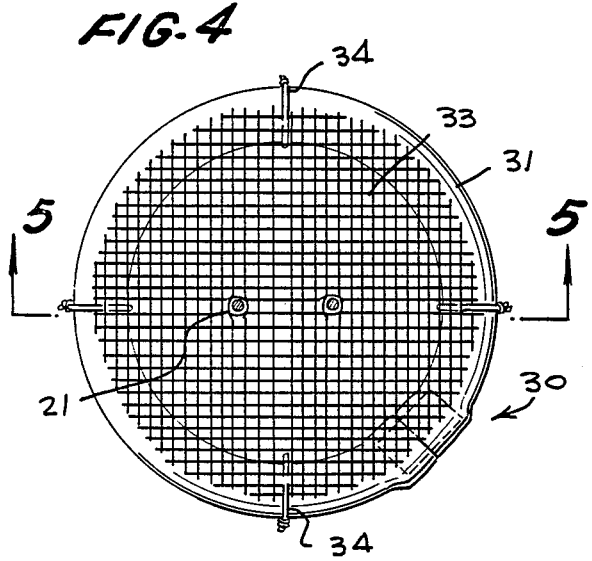
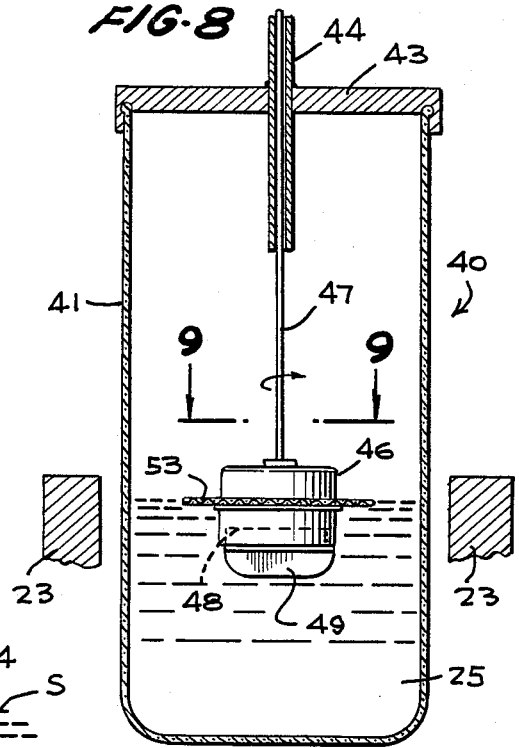
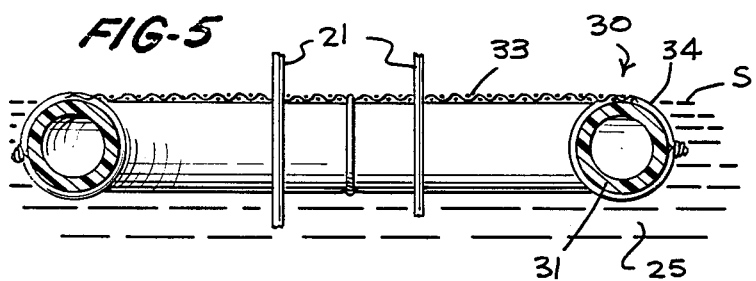
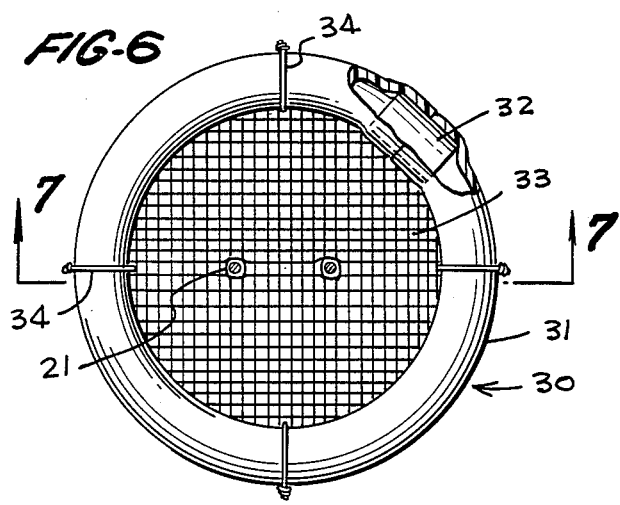
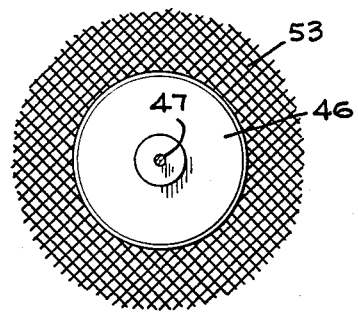
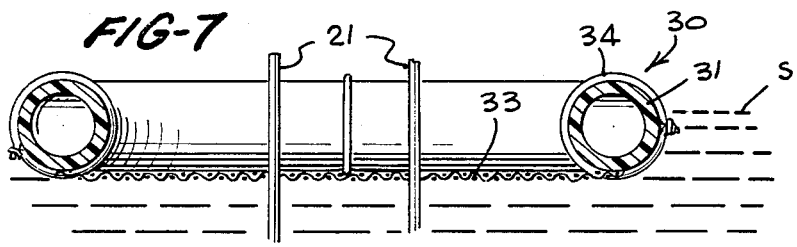

BIOREACTOR APPARATUS WITH SURFACE AERATOR SCREEN

BACKGROUND OF THE INVENTION

The present invention relates to a bioreactor for growing cell culture.

Cell culture has greatly increased in recent years due to two advances: (1) micro carriers and (2) hybridomas.

Mammalian cells can be classified as being either anchorage dependant or suspension cells. Normal cells (as distinct from cancer cells) are "anchorage dependent"; they need a hydrophilic solid surface to attach themselves to, before they will propagate themselves by division. They are grown on the inside of horizontal cylindrical glass roller bottles; this is a tedious batch operation unsuitable for mass production. However, by growing anchorage dependent cells on minute solid particles ("micro carriers") kept in suspension in a stirred vessel, large scale production becomes possible. Hybridoma cells are hybrids produced by fusing myelona (cancer cells) with cells which express monoclonal antibodies; these hydrids are not anchorage dependent and do not require micro carriers to keep them in suspension.

Both types of cells require gentle stirring. The initial stage of "plating" normal cells on micro carriers is especially critical. Both types of cells require a liquid medium containing nutrients and dissolved oxygen and carbon dioxide. In the past these gases have been supplied from the head space above the liquid medium which half fills a flask. But such a method of oxygenation becomes insufficient when the volume of the liquid medium is greater than about 3 liters.

The problem of oxygenation has become a critical one. Several methods of overcoming this difficulty have been used:

(1) "Sparging" which is the introduction of gases through a sparger at the bottom of the flask;

(2) Introduction of gas through a permeable membrane or tube (immersed in the medium), such as silicon rubber or porous polypropylene, which allows the gas to diffuse into the medium without formation of bubbles.

(3) Injecting air into the head space through outlets placed directly over the liquid surface.

(4) Providing a revolving solid blade at the liquid surface for surface aeration.

The first two of these solutions suffer from severe disadvantages. Sparging produces foam; the permeable tube requires an excessive length of tubing which interferes with the circulation in the flask, and is difficult to clean. Injecting air requires more complex equipment, and the revolving solid blade achieves less than desireable oxygen transfer.

SUMMARY OF THE INVENTION

There is provided a bioreactor for cell culture medium including a flask or vessel which is partially filled with liquid cell culture medium, thereby leaving a head space above the liquid culture medium, and providing a liquid-air interface at the surface of the liquid culture medium. An impeller is provided for causing circulation of the liquid culture medium to and from the surface, and there is provided a screen or foraminous surface agitator to cause non-laminar flow of at least part of the liquid culture medium in the surface region. In one form of an apparatus in accordance with the present invention there is provided a buoyant body having a screen attached to it, positioned generally horizontally and at or adjacent to the surface of the liquid culture medium, and in the liquid culture medium, the screen being rotated about a vertical axis, so that the rotation of the screen causes both the circulation of the liquid culture medium to and from the surface thereof, as well as causing agitation of the liquid culture medium at the surface thereof so as to provide non-laminar flow of the liquid culture medium in the surface region. The screen is caused to rotate by a shaft formed by two vertically extending, spaced and parallel rods which are supported by a bearing in a lid on the vessel, the lid supporting electro-magnets, and the rods carrying a generally horizontally extending magnet, the electro magnets and the magnet causing rotation of the shaft formed by the parallel rods. Due to the passage of the rods through spaced openings in the screen, and the support of the screen by the buoyant body, the position of the buoyant body and screen may accommodate to different levels of liquid culture medium in the flask, while providing for a driving or torque-transmitting conneciton between the rods and the screen at any level of the liquid culture medium.

In another embodiment, a buoyant body is provided having a magnet within it and having an impeller supported by the buoyant body, preferably beneath the body. The electro-magnet coils are positioned exteriorly of the vessel for effecting rotation of the buoyant body and impeller, by interaction of the field thereof with the magnet within the impeller. Extending upwardly from the buoyant body is a rod which is guided for rotational and translational movement within a vertical tube carried by the lid of the vessel. Agitation of the liquid in the surface region of the liquid culture medium is provided by a screen, preferably of annular formation, attached to the buoyant body and extending generally horizontally therefrom, and located on the buoyant body so that it is in the surface region of the liquid culture medium.

Among the objects of the present invention are the provision of an improved bioreactor apparatus, to provide an improved bioreactor apparatus in which there is enhanced oxygen transfer with resulting increased cell growth, to provide a bioreactor apparatus which transfer, large quantities of oxygen without requiring the introduction of oxygen or air by pressurized air and conduits, the provision of a bioreactor apparatus which provides for enhanced oxygenation without damage to the cells, and to provide a bioreactor apparatus which, while providing for enhanced oxygenation, avoids foaming, mechanical complexity and attendant expenses, and cell damage.

Other objects and many of the attendant advantages of the present invention will be readily understood from the following specification and claims, and from the appended drawings.

BRIEF DESCRIPTION OF THE DRAWINGS

FIG. 4 is a cross-sectional view taken on the line 4—4 of FIG. 1.

FIG. 5 is a cross-sectional view taken on the line of 5—5 of FIG. 4.

FIG. 6 is a view similar to FIG. 4, of an alternate embodiment.

FIG. 7 is a cross-sectional view taken on the line 7—7 of FIG. 6.

FIG. 8 is a cross-sectional view of another embodiment of a bioreactor in accordance with the present invention.

FIG. 9 is a cross-sectional view taken on the line 9—9 of FIG. 8.

DESCRIPTION OF THE PREFERRED EMBODIMENTS

Figure 1:
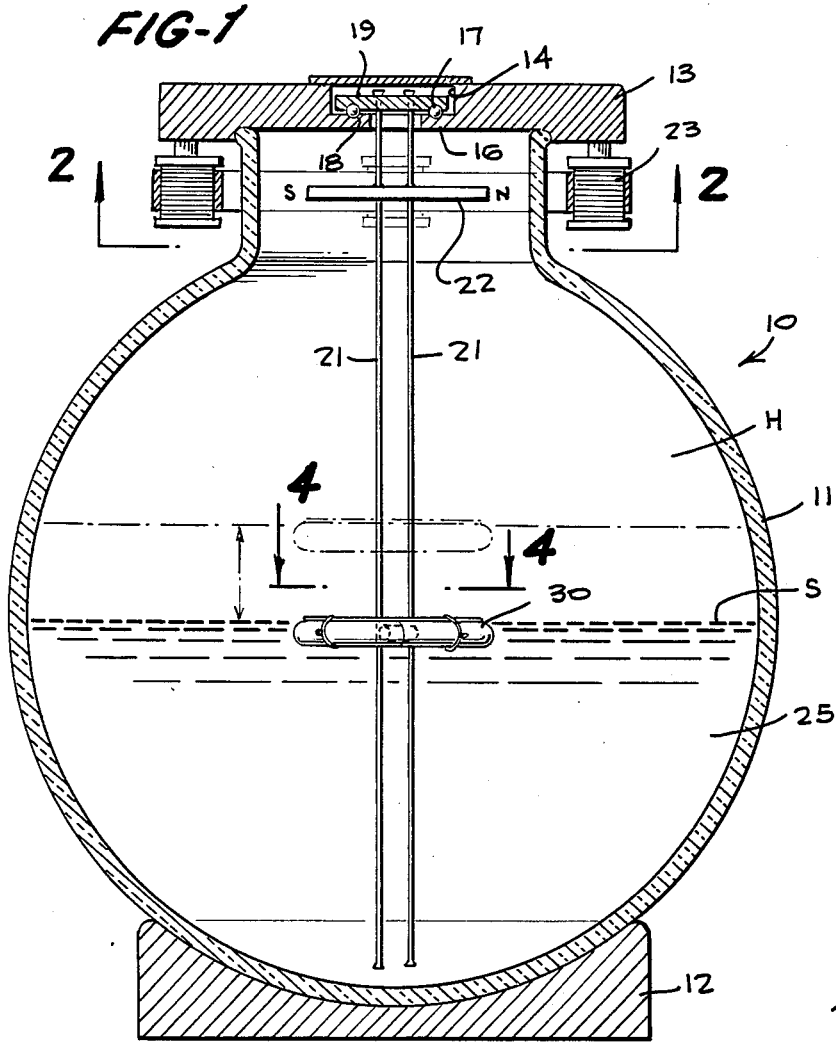
FIG. 1 is a cross-sectional view of an improved bioreactor in accordance with the present invention.

Referring now to the drawings, wherein like or corresponding references numbers are used to designate like or corresponding parts throughout the several views, there is shown in FIG. 1 a bioreactor 10 including an open-mouthed vessel 11 resting on a suitable support 12. A lid 13 is provided for closing the mouth of vessel or flask 11, having a central recess 14 providing a shoulder 16. An annular series of balls 17 rests in an annular groove 18 in shoulder 16, and a bearing support disk 19 is supported by the balls 17.

Depending from the bearing support disk 19 are a pair of spaced, parallel rods 21, to which is connected a magnet 22 in the form of a bar, which extends generally horizontally.

Figure 2:
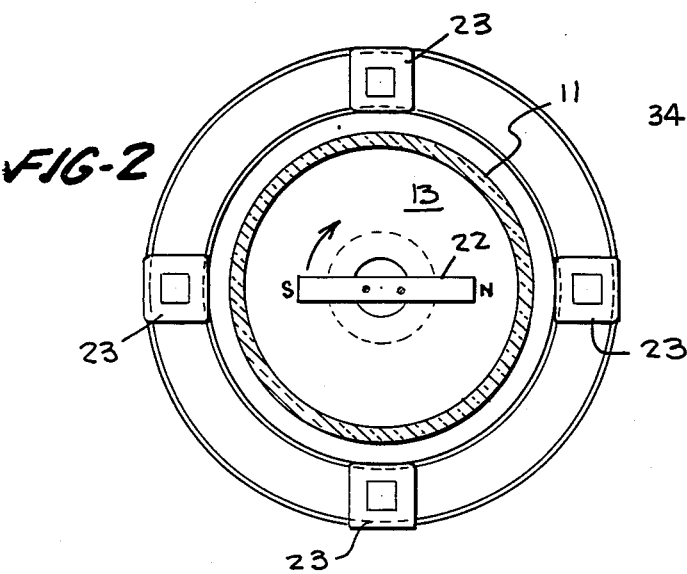
FIG. 2 is a cross-secctional view taken on the line 2—2 of FIG. 1.

Depending from and carried by the lid 13 are a plurality of electro-magnets 23. The electro magnets 23 may be sequentially energized, as in the manner disclosed in de Bruyne U.S. Pat. No. 4,465,377, to cause rotation of magnet 22, and thereby of the rods 21. As seen in FIG. 2, there are preferably four electro magnets 23, arranged at intervals of 90 degrees about the axis of the vessel or flask 11.

Referring again to FIG. 1, the vessel or flask 11 is partially filled with liquid cell culture medium 25, so that there is thereby provided a liquid-air interface at surface S of the liquid medium 25, above which is a head space H which contains air, in known manner; other gas comprising or containing oxygen may be utilized.

Figure 3:
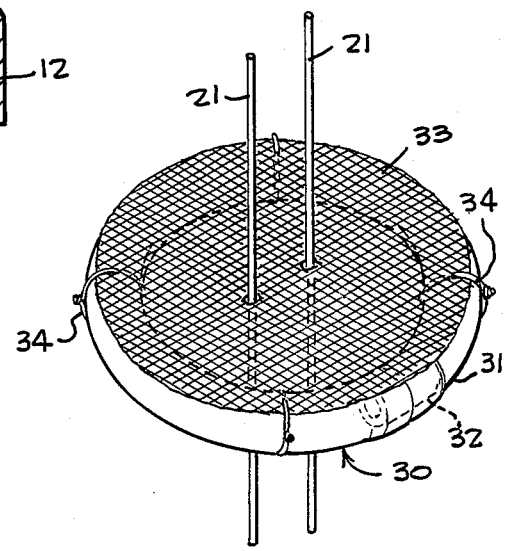
FIG. 3 is a perspective view of a part of the apparatus of FIG. 1.

In FIG. 3, there is shown a buoyant structure which includes a float or buoyant body 30, in the form of a tube 31 having its ends connected by a nipple 32. The annular or ring-shaped tube 31 has secured to it a screen 33, which is preferably in the form of a disk, and which is secured to the tube 31 by a plurality of wires 34 which encircle the tube 31 and pass through the screen 33. Also passing through the screen 33 are the spaced, parallel and vertically extending rods 21.

As seen in FIG. 4, the float 30 comprises the tube 31 which is of ring-like configuration, and on which is the screen 33 having a radial extent not in excess of the radius of the ring-like tube 31, although the radial extent of screen 33 may be greater or less than that illustrated in FIG. 4.

As shown in FIG. 5, the screen 31 is immersed in the liquid cell culture medium 25 at or adjacent the surface S thereof, it being understood that the locus of screen 33 relative to the surface S may be adjusted by adding or removing weights, such as the plurality of wires 34.

In operation, with the flask or vessel 11 partially filled with liquid cell culture medium 25 as shown in FIG. 1, the electro magnets are energized so as to cause rotation of magnet 22, and of the spaced, parallel and vertically extending rods 21, supported by the bearing support disk 19 and the balls 17. Rotation of the rods 21 will cause rotation of the float 30, and the rotation of the screen 33 will cause both circulatory movement of the liquid cell culture medium 25 and agitation of a portion of the surface region of the liquid cell culture medium 25. More particularly, rotation of float 30, including screen 33, will cause liquid cell culture medium 25 in the surface region to flow outwardly along the surface, and then downwardly along the walls of flask 11, towards the bottom, central part of the flask 11, and then inwardly and upwardly, thereby providing circulation of substantially the entire body of the liquid cell culture medium 25 to and from surface S. In addition, the agitation of a substantial horizontal part or expanse of the surface region by the screen 30 will cause non-laminar flow of liquid in at least part of the surface region. This will result in elemental portions of the liquid cell culture medium moving to the surface S, then moving away from the surface S, and then again moving to the surface S, so that there is enhanced exposure of the liquid cell culture medium on a repetitive basis to the oxygen-containing gas occupying the head space H.

Referring to FIG. 6, there is shown a view similar to FIG. 4, but in this embodiment, the screen 33 is located (see also FIG. 7) below the tube 31. Screen 33 is secured to the tube 31 by a plurality of wires 34, and is penetrated by the rods 21 in the same manner as in the embodiment of FIGS. 1–5. As will be seen from FIG. 7, the screen 33 is at a somewhat lower level, relative to the surface S, than the screen 33 in the embodiment of FIGS. 1–5. The operation of the embodiment of FIGS. 6 and 7 is substantially the same as the operation of the embodiment of FIGS. 1–5 although with less oxygen transfer.

Referring now to FIGS. 8 and 9, there is shown an alternate construction of a bioreactor, generally designated 40 and including a cylindrical open-mouth flask 41 having a lid 43 for substantially closing flask 41, through which lid 43 passes a generally vertically extending guide tube 44. A hollow floating body 46 has a guide rod 47 extending from the upper surface thereof, and into the guide tube 44. A magnet 48 is carried within the floating body 46 and exteriorly of the flask 41 are a plurality of electro-magnets 23, or other equivalent structures, for generating a moving electro-magnetic field to cause rotation of the magnet 48. Carried by the floating body 46 is an impeller or vane 49 which, upon rotation of it, with the floating body 46, causes circulation of the liquid culture medium 25 which partially fills the flask 41. An annular screen 53, see also FIG. 9, is attached to the floating body 46, so as to lie in the liquid cell culture medium 25 in the surface region thereof.

Energization of the electro magnets 23 causes the magnet 48 to rotate, to thereby cause rotation of the floating body 46. The guide shaft 47, guided by guide tube 44, causes the axis of the floating body 46 to remain substantially coincident with the axis of flask 41 and guide tube 44, with different quantities of liquid cell culture medium 25 in the flask 41. As will be understood, the electro-magnets 23 or other equivalent structure will generate a moving magnetic field for interaction with the magnet 48 at whatever operative level the magnet 48 occupies, which level is dependant upon the quantity of liquid cell culture medium 25 within the flask 41.

Rotation of the floating body 46 will cause the impeller 49 to be rotated, and this will effect circulation of the liquid cell culture medium 25 to and from the surface S thereof. Thus, in known manner, substantially the entire volume of the liquid cell culture medium 25 is circulated to and from the surface S. Oxygen transfer into the liquid cell culture medium 25 is enhanced and increased by the agitation effected by the screen 53, which causes non-laminar flow of at least a portion of the liquid cell culture medium in the surface region thereof.

The rate of solution of oxygen in cell culture medium equals $(K_L 2a)(C^* + C)/t$, where $C^*$ is the saturation concentration of oxygen in the liquid and $(K_L a)$ is the oxygen transfer rate or coefficient, which can be determined from the formula $-K_L a = \ln(C^* - C)/t$, Where $C^*$ is the concentration at saturation in mg per liter, and C is the concentration at time t.

Experiments have shown that with the structure of FIGS. 1–5, the mass transfer coefficient equals 4.0 hours $^{-1}$, whereas with the arrangement of FIGS. 6 and 7, other factors remaining the same, the mass transfer coefficient was 2.6 hours $^{-1}$.

Tests were also conducted on the apparatus shown in FIGS. 8 and 9, using 2500 milliliters saline water at 37° C., with the impeller being rotated at a speed of 300 revolutions per minute. The following results were obtained for different diameters of the screen, the first test being of the structure shown in FIG. 8, but without any screen in place:

| Outside diameter of screen | $K_L{}^a$ Hour $^{-1}$ |
|---|---|
| 0 (no screen) | 1.84 |
| 60 mm | 3.84 |
| 65 mm | 5.20 |
| 70 mm | 5.84 |
| 75 mm | 6.64 |
| 80 mm | 8.24 |

The screen used in all of the experiments was conventional 16 mesh screening.

The bioreactors herein disclosed are exemplary, and, as will be understood, they provide for both circulation and enhanced oxygenation by agitation or the creation of non-laminar flow in the surface region of the liquid cell culture medium. The screen or discontinuous body which generates non-laminar flow of the liquid in the surface region may be either movable or fixed. As herein illustrated, the structure or body is rotated, and is connected with or supported by a buoyant body. The non-laminar flow generator may be supported by a structure which is not buoyant so long as it is at least partially in the surface region of the liquid cell culture medium. The structure may be rotated, or reciprocated horizontally, or reciprocated vertically or given some other motion or combination of motions which will have the effect of causing non-laminar flow in at least part of the surface region. While the bodies herein illustrated are screens of either disk or annular configuration, the screens may be segmented so as to present a series of slightly inclined vanes, similar to turbine blades, or other configuration. The body need not be a screen, but, for example, could be a series of spaced wires or rods, could be a comb-like construction, could be provided by a multiplicity of small, elemental bodies, such as spheres, blocks, etc. Further, the body or bodies providing the non-laminar flow need not be moving, but may be fixed, as by providing a barrier or barriers which so interfere with the flow in the surface region that that flow is caused to be non-laminar. The structures shown in the drawing are considered to be among those which are the most effective and most efficient, particularly that shown in FIGS. 8 and 9.

The herein described apparatus does not require the pumping or introduction of air or oxygen into the apparatus and the liquid cell culture medium, thereby providing enhanced oxygenation with an inexpensive and simple apparatus. The circulation and agitation herein above provided by the disclosed apparatus is not voilent, and is sufficiently gentle so that there is no significant harm to the cells.

It will be obvious to those skilled in the art that various changes may be made without departing from the spirit of the invention, and therefore the invention is not limited to that shown in the drawings and described in the specification, but only as indicated in the appended claims.

I claim:

1. A bioreactor for growing cell culture by liquid cell culture medium circulation and surface agitation comprising a substantially closed flask holding a body of liquid culture medium which partially fills the flask providing a liquid surface with a gas head space above the liquid surface with a liquid-gas interface at the liquid surface, means for causing circulation of the liquid culture medium from beneath the liquid culture medium surface up to the liquid culture medium surface, then along the liquid-gas interface at the culture medium surface and then downwardly from the liquid culture medium surface without entry into the head space, means for agitating liquid culture medium in said flask in a horizontal expanse of the surface region comprising a screen in said liquid culture medium adjacent the surface thereof, said screen extending generally horizontally and at least partially in the surface region of the culture medium, and means for rotating said screen in a substantially horizontal plane, whereby to provide a high oxygen transfer rate into the liquid culture medium from the head space.

2. The bioreactor of claim 1, and buoyant means for supporting said screen.

3. The bioreactor of claim 1, said rotating means extending through said screen and having a torque transmitting and axially sliding connection therewith.

4. The bioreactor of claim 1, wherein said circulating means comprises an impeller and means for rotating said impeller.

5. The bioreactor of claim 4, and buoyant means for supporting said screen, said means for rotating said impeller comprising a magnet carried by said buoyant means.

6. The bioreactor of claim 5, and means for guiding said buoyant means in a vertical path as the level of said body of liquid culture medium changes.

7. A bioreactor comprising a flask for holding a body of liquid culture medium which partially fills the flask providing a liquid surface with a gas head space above the surface, means for causing circulation of the liquid culture medium to and from the surface of the body of liquid culture medium, a screen in said liquid culture medium adjacent the surface thereof, and means for rotating said screen in a substantially horizontal plane, whereby to provide a high oxygen transfer rate into the liquid culture medium from the head space, a buoyant body, said means for causing circulation comprising an impeller supported by said buoyant body, and a magnet carried by said buoyant body; said screen carried by said buoyant body.

8. A bioreactor for growing cell culture by liquid cell culture medium circulation and surface agitation comprising:
   (a) a substantially closed vessel partially filled with liquid with a gas head space above the liquid surface with a liquid-gas interface at the liquid surface,
   (b) means for causing circulation of liquid along the surface thereof from beneath the liquid surface up to the liquid surface, then along the liquid-gas interface at the liquid surface and then downwardly from the liquid surface without entry into the gas head space above the liquid surface, and
   (c) means for causing non-laminar flow of at least some of said liquid in the surface region thereof at the liquid-gas interface, comprising a generally planar discontinuous body in said liquid culture medium adjacent the surface thereof, and means for moving said body in said liquid, whereby to enhance oxygen transfer into said liquid.

9. The bioreactor of claim 8, said body being a screen.

10. The bioreactor of claim 8 and means for maintaining said body adjacent the liquid surface with changes in the level of the liquid surface in said vessel.

11. A bioreactor for growing cell culture by liquid cell culture medium circulation and surface agitation for stirring and oxygenating cell culture medium comprising:
   a substantially closed flask partially filled with cell culture medium to thereby provide a liquid culture medium surface and a head space for gas comprising oxygen above said surface with a liquid-gas interface at the liquid surface,
   means for causing circulation of the cell culture medium in said flask from beneath the cell culture medium surface up to the cell culture medium surface, then along the cell culture medium-gas interface at the liquid culture medium surface and then downwardly from the cell culture medium surface without entry into the gas head space above the surface of the cell culture medium to thereby expose cells in said culture medium to the oxygen in said head space at the liquid-gas interface, and
   means for causing non-laminar flow of a substantial horizontal part of the surface region of the body of cell culture medium comprising a discontinuous body and means for supporting said discontinuous body at least in part in the surface region of the cell culture medium.

12. The bioreactor of claim 11, wherein said means for supporting said discontinuous body comprises a buoyant body, said discontinuous body extending outwardly from said buoyant body, and means for moving said discontinuous body comprising a magnet in said buoyant body.

13. The bioreactor of claim 12, said means for causing circulation comprising an impeller carried by said buoyant body.

* * * * *